United States Patent
Leiden et al.

(10) Patent No.: US 6,436,907 B1
(45) Date of Patent: *Aug. 20, 2002

(54) ADENOVIRUS-MEDICATED GENE TRANSFER TO CARDIAC AND VASCULAR SMOOTH MUSCLE

(75) Inventors: Jeffrey M. Leiden, Glencoe, IL (US); Eliav Barr, St. David's, PA (US)

(73) Assignee: Arch Development Corporation, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/186,968

(22) Filed: Nov. 5, 1998

Related U.S. Application Data

(63) Continuation of application No. 09/972,831, filed on Nov. 18, 1997, which is a continuation of application No. 08/417,459, filed on Apr. 5, 1995, now abandoned, which is a continuation of application No. 07/977,496, filed on Nov. 18, 1992, now abandoned.

(51) Int. Cl.$^7$ .................. A01N 43/04; A01N 63/00; C07H 21/04; C12N 15/00; C12N 15/63
(52) U.S. Cl. .............. 514/44; 435/320.1; 435/325; 435/455; 536/23.5; 424/93.21
(58) Field of Search ............ 514/44, 2; 536/23.1, 536/23.5; 435/320.1, 455, 325; 530/350; 424/93.21

(56) References Cited

U.S. PATENT DOCUMENTS

| | | | |
|---|---|---|---|
| 4,920,209 A | | 4/1990 | Davis et al. ............. 435/235 |
| 5,328,470 A | * | 7/1994 | Nabel et al. ............. 604/101 |
| 5,693,622 A | | 12/1997 | Wolff et al. ............. 514/44 |
| 5,698,531 A | | 12/1997 | Nabel et al. ............. 514/44 |
| 5,707,969 A | | 1/1998 | Nabel et al. ............. 514/44 |

FOREIGN PATENT DOCUMENTS

| | | |
|---|---|---|
| AU | 666142 | 7/1993 |
| WO | WO 91/05180 | 5/1990 |
| WO | WO 90/06997 | 6/1990 |
| WO | WO 91/15580 | 10/1991 |
| WO | WO 93/06223 | 4/1993 |

OTHER PUBLICATIONS

E. Marshal, Science, vol. 269, p. 1052–1053, Aug. 1995.*
Nabel et al., Annals of the New York Academy of Sciences, 714:247–25, Apr. 1994.*
Willard et al., Circulation, vol. 86(4), suppl. 1, p. 1–473, Nov. 1992.*
Stratford–Perricaudet et al., J. Clin. Invest., 90: 626–630, Aug. 1992.*
Clesham et al., Circulation Research, vol. 79 (6), p. 1188–1195, 1996.*
Fett et al., Biochemical and Biophysical Research Communication, vol. 146, No. 3, p. 1122–1131, 1987.*

Bonnerot et al. "A β–galactosidase hybrid protein targeted to nuclei as a marker for developmental studies", Proc. Nat'l. Acad. Sci. USA (1987) vol. 84, pp. 6795–6799.
Bühler et al., "Characterization of the Murine Cytomegalovirus Early Transcription Unit e1 That is Induced by Immediate–Early Proteins", J. Virol. (1990) vol. 64, pp. 1907–1919.
Connolly, "Vascular Permeability Factor: A Unique Regulator of Blood Vessel Function", J. Cell Biochem.. (Nov., 1991) vol. 47(3), pp. 219–223.
Crumley et al., "The Gene for Human Acidic Fibroblast Growth Factor Encodes Two Upstream Exons Alternatively Spliced to the First Coding Exon", Biochem. Biophys. Res. Commun. (1990), vol. 171, pp. 7–13.
Folkman and Klagsbrun, "Angiogenic Factors", Science, (Jan. 23, 1997); vol. 235 (4787), pp. 442–447.
Giordano et al., "Intracoronary gene transfer of fibroblast growth factor–5 increases blood flow and contractile function in an ischemic region of the heart", Nature Med. (1996), vol. 2, pp. 534–539.
Kitsis et al., "Hormonal modulation of a gene injected into rat heart in vivo", Proc. Nat'l. Acad. Sci. USA (1991)vol. 88, pp. 4138–4142.
Kurachi et al., "Sequence of the cDNA and Gene for Angiogenin, a Human Angiogenesis Factor", Biochemistry (1985) vol. 24, pp. 5494–5499.
Kurokawa et al., "Cloning and expression of cDNA encoding human basic fibroblast growth factor", FEBS Lett. (1987) vol. 213, pp. 189–194.
Lehner et al., "Comparative Sequence Analysis of Human Cytomegalovirus Strains", J. Clin. Microbiol (1990) vol. 29, pp. 2494–2502.
Leung et al., "Vascular Endothelial Growth Factor Is a Secreted Angiogenic Mitogen", Science (1989), vol. 246, pp. 1306–1309.
Mackem and Roizman, "Structural Features of the Herpes Simplex Virus α Gene 4.0, and 27 Promoter–Regulatory Sequences Which Confer α Regulation on Chimeric Thymidine Kinase Genes", J. Virol. (1982) vol. 44, pp. 939–949.
Schneider and French. "The Advent of Adenovirus Gene Therapy for Cardiovascular Disease", Circulation (1993) vol. 88, pp. 1937–1942.

(List continued on next page.)

Primary Examiner—Deborah J. R. Clark
Assistant Examiner—Shin-Lin Chen
(74) Attorney, Agent, or Firm—Hale and Dorr LLP

(57) ABSTRACT

The present invention relates to the use of adenovirus-mediated gene transfer to regulate function in cardiac and vascular smooth muscle cells. A recombinant adenovirus comprising a DNA sequence that codes for a gene product is delivered to a cardiac or vascular smooth muscle cell and the cell is maintained until that gene product is expressed. Delivery is direct injection into a muscle cell or infusing a pharmaceutical composition containing an adenovirus virus vector construct intravascularly.

34 Claims, No Drawings

OTHER PUBLICATIONS

Tio, et al. "Intramyocardial Gene Therapy with Naked DNA Encoding Vascular Endothelial Growth Factor Improves Collateral Flow to Ischemic Myocardium," Human gene Therapy, (1999) vol. 10, pp. 2953–2960.

Mack et al., "Biologic Bypass with the Use of Adenovirus–Mediated Gene Transfer of the Complementary Deoxyribonucleic Acid for Vascular Endothelial Growth Factor 121 Improves Myocardial Perfusion and Function in the Ischemic porcine Heart," (1998) J. Thoracic and Cardivascular Surgery, vol. 115, pp. 168–177.

Blank et al, Elements of the Smooth Muscle α–Action Promoter Required in Cis for Transcriptional Activation in Smooth Muscle, J. Biol. Chem., 267:984–989, 1992.

Bloch et al, Structural Organization and Chromosomal Assignment of the Gene Encoding Endothelin, J. Biol. Chem., 264:10851–10857, 1989.

Buttrick et al, Behavior of Genes Directly Injected into the Rat Heart in Vivo, Circ. Res., 70:193–198, 1992.

Chang et al, Replication–Deficient Andenovirus Encoding Rb Reduces Smooth Muscle Cell and Neointima Formation, Science, 267:518, 1995.

Johnson et al, Muscle Creatine Kinase Sequence Elements Regulating Skeletal and Cardiac Muscle Expression in Transgenic Mice, Mol. Cell. Biol., 9: 3393–3399, 1989.

Le Marchand, Adenovirus–mediated Transfer of a Recombinant Human $\alpha_1$–antitrypsin cDNA to Human Endothelial Cells, PNAS 89:6482–6486 (1992).

Leinwand et al., Gene Transfer into Cardiac Myocytes in vivo, TCM, 1:271–276 (1991).

Lin et al, Expression of Recombinant Genes in Myocardium in Vivo After Direct Injection of DNA, Circulation 82:2217–2221, 1990.

Parmacek, et al., "Identification and characterization of a cardiac–specific transcriptional regulatory element in the slow/cardiac troponin C gene", Biol. Abstracts, 94:16544, 1992.

Parmacek et al, The Structure and Regulation of Expression of the Murine Fast Skeletal Troponin C Gene, J. Biol. Chem., 265:15970–15976, 1990.

Parmacek et al, Identification and Characterization of Cardiac–Specification Transcriptional Regulatory Element, Mol Cell Biol., 12:1967–1976, 1992.

Quantin et al, Adenavirus as an Expression Vector in Muscle Cell, Application to Distrophin, Colloque Inserm (Human Gene Transfer–Intern Workshop), 219:271–272, 1991.

Rosenfeld et al, Adenovirus–Mediated Transfer of a Recombinant $\alpha 1$–Antitrypsin Gene to the Lung Epithelium in Vivo, Sciences 252: 431–434, 1991.

Rosenfield et al, In Vivo Transfer of the Human Cystic Fibrosis Transmembrane Conductance Regulator Gene to the Airway Epithelium, Cell., 68:143–155, 1992.

Stratford–Perricaudet et al, Widespread Long–Term Gene Transfer to Mouse Skeletal Muscles and Heart, J. Clin. Invest., 90: 626–630, 1992.

Stratford–Perricaudet et al, Evaluation of the Transfer and Expression in Mice of an Enzyme–Encoding Gene Using a Human Adenovirus Vector, Hum. Gene. Ther., 1:241–256, 1990.

Stratford–Perrcaudet et al, Gene Transfer into Animal: the Promise of Adenovirus, Colloque Inserm (Human Gene Transfer–Intern Workshop), 219:51–61, 1991.

VanDoren, K. and Gluzman, Y., Efficient Transformation of Human Fibroblasts by Adenovirus–Simian Virus 40 Recombinants, Mol. Cell. Biol., 4:1653–1656, 1984.

Van Doren et al, Infection of Eucaryotic Cells by Helper–Independent Recombinant Adenoviruses: Early region 1 Is Not Obligatory for Integration of Viral DNA, J. Virol., 50:606–614, 1984.

Walsh et al, Two Nuclear Factors Complete for the Skeletal Muscle Actin Promoter, J. Biol. Chem. 262: 9429–9432, 1987.

Wolfe et al, Herpes Virus Vector Gene Transfer and Expression of β–glucuronidase in the Central nervous System of MPS VII Mice, Nature Genetics, 1: 379–384, 1992.

Yi et al, Rabbit Muscle Creatine Kinase: Genomic Cloning, Sequencing, and Analysis of Upstream Sequences Important for Expression in Myocytes, Nucleic Acids Res., 19:3027–3033, 1991.

Willard et al., Circulation, vol. 86 (4) suppl. 1, p. 1–473.

* cited by examiner

ADENOVIRUS-MEDICATED GENE TRANSFER TO CARDIAC AND VASCULAR SMOOTH MUSCLE

This application is a continuation of U.S. Ser. No. 08/972,831, filed Nov. 18, 1997, pending, which is a continuation of U.S. Ser. No. 08/417,459, filed Apr. 5, 1995, abandoned, which is a continuation of U.S. Ser. No. 07/977,496, filed Nov. 18, 1992, abandoned.

TECHNICAL FIELD OF THE INVENTION

The present invention relates to a process of regulating gene transcription and gene product expression in cardiac and vascular smooth muscle. More particularly, a process of the present invention relates to adenovirus vector mediated delivery of genes to cardiac muscle and to coronary vascular smooth muscle.

BACKGROUND OF THE INVENTION

Somatic gene therapy can be defined as the ability to program the expression of foreign genes in non-germ line (i.e., non-sperm and egg) cells of an animal. Methods of somatic gene therapy can be divided into two categories. Ex vivo gene therapy involving the removal of cells from a host organism, transfection a foreign gene into those cells, and reimplantation or transplantation of the transformed or transgenic cells back into a recipient host. In contrast, in vivo gene therapy involves transfection of a foreign gene directly into cells of a recipient host without the need for prior removal of those cells from the host.

The utility of somatic gene therapy for human subjects is dependent upon a number of factors. First, the transfection method must be efficient. Second, expression of the foreign gene should be localized to specific target tissues. Third, a given transfection process should be associated with a minimal risk of mutating the host cells and of causing a persistent infection of the host organism.

Several possible strategies to introduce genes into tissues of the body have been employed in the past (Stratford-Perricaudet et al., 1990; Rosenfeld et al., 1992; Wolfe et al., 1992). Procedures to introduce foreign genes into cells include direct transfection (Davis et al., 1986) and retroviral gene transfer (Dichek et al., 1991; Wilson et al., 1988a; Wilson et al., 1988b; Kay et al., 1992). In some cases, genetically altered cells have been reintroduced into animals (Dichek et al., 1991; Roy Chowdhury et al., 1991) where their continued function has been monitored for variable periods of time.

Recently, adenovirus-mediated gene transfer has been investigated as a means of somatic gene therapy into eukaryotic cells and into whole animals (van Doren et al., 1984a; van Doren et al., 1984b; Ghosh-Choudhury and Graham, 1987; Stratford-Perricaudet et al., 1990; Rosenfeld et al., 1991; Rosenfeld et al., 1992). A problem with adenovirus mediated gene transfer is the low level of gene product expression in target cells and a resultant lack of a functional effect.

Although adenovirus-mediated gene transfer has been used to treat ornithine transcarbamylase (OTC) deficiency in newborn mice, the expression of the ornithine transcarbamylase enzyme in the virus infected mice was typically at or below expression levels in normal mice with the result that the defect was only partially corrected (Stratford-Perricaudet et al., 1990). On the basis of those data, one would not expect that adenovirus-mediated gene transfer would be applicable to treatment of a disease requiring an overexpression of a gene product.

Adenovirus mediated transfer of the gene for cystic fibrosis transmembrane conductance regulator (CFTR) into the pulmonary epithelium of cotton rats has been attempted, although it has not been possible to assess the biological activity of the transferred gene because there was no physiologic effect of gene transfer despite expression of the CFRR protein in lung airway cells (Rosenfeld et al., 1992). Still further, lung expression of $\alpha$1-antitrypsin protein was not associated with a physiologic effect (Rosenfeld et al., 1991). Taken together, those data do not demonstrate that adenovirus can transfer genes into cells and direct the expression of sufficient protein to achieve a physiologically relevant effect.

Targeting somatic gene therapy to cardiac tissue can be used in the treatment of a number of inherited and acquired cardiac diseases such as genetic disorders of myocardial cells. By way of example, injection of the normal dystrophin cDNA can be used to correct the defects in cardiac contractility seen in patients with Duchenne's muscular dystrophy. By way of further example, the injection of plasmids encoding recombinant angiogenesis factors directly into the left ventricular wall can be used to stimulate new collateral circulation in areas of chronically ischemic myocardium. Somatic gene therapy can also be used to directly study the molecular mechanisms regulating cardiac myocyte gene expression both during cardiac myogeneses and in a variety of pathophysiologic states such as cardiac hypertrophy.

As many as 1.5 million patients per year in the U.S. suffer a myocardial infarction (MI). Many millions more suffer from syndromes of chronic myocardial ischemia due to large and small vessel coronary atherosclerosis. Many of these patients will benefit from the ability to stimulate collateral vessel formation in areas of ischemic myocardium. Adenovirus mediator gene transfer methods provide an alternative approach to the current methods of coronary artery bypass and percutaneous transluminal coronary angioplasty. In particular, many patients have such revere and diffuse atherosclerosis that they are not candidates for CABG or PTCA. Thus far, there has been no approach which has successfully stimulated collateral vessel formation in areas of ischemic myocardium.

Previous approaches have all utilized in vitro transfection protocols into neonatal cardiocytes or transgenic approaches in mice. Such studies are complicated by the fact that neonatal cardiocytes may not reflect the in vivo situation and by the fact that neonatal cardiocytes have an extremely limited life span in tissue culture and cannot be incorporated into the heart. Moreover, transgenic approaches are lengthy (requiring 6 months to 1 year) technically difficult and expensive. The gene transfer approach of the present invention provides a solution to these problems and provides for the stable expression of recombinant gene products in cardiac myocytes in vivo.

BRIEF SUMMARY OF THE INVENTION

The present invention relates to a process of regulating the function of a cardiac or a vascular smooth muscle cell, whether that cell be in vivo or in vitro. Muscle cell function is regulated by altering the transcription of genes and changes in the production of a gene transcription product such as a polynucleotide or a polypeptide. That polynucleotide or polypeptide interacts with the cardiac or vascular smooth muscle cell to regulate function of that cell.

In one aspect, therefore, the present invention provides a process of regulating expression of a gene product in a cardiac or a vascular smooth muscle cell, which process comprises the steps of:

a) delivering to the muscle cell an adenovirus vector construct comprising a coding sequence that encodes the gene product, which vector drives expression of the gene product in the muscle cell; and b) maintaining the muscle cell under physiological conditions sufficient for the gene product to be expressed in the muscle cell.

An adenovirus used in a process of the present invention is replication-defective. Preferably, a replication-defective adenovirus lacks the early gene region E1 or the early gene regions E1 and E3. A preferred adenovirus is a type 5 adenovirus and a coding sequence is preferably flanked by adenovirus type 5 sequences.

In a preferred embodiment, a coding sequence is operatively linked to an enhancer-promoter other than an adenovirus enhancer-promoter. A preferred enhancer-promoter is a CMV promoter, a SV40 early promoter, a RSV promoter or a MCK enhancer. More preferably, an enhancer-promoter is a tissue specific enhancer-promoter. A preferred cardiac muscle specific enhancer-promoter is a cTNC promoter. A preferred vascular smooth muscle specific enhancer-promoter is an endothelin promoter or a smooth muscle α-actin promoter.

A coding sequence is operatively linked to a transcription-terminating region. A preferred transcription-terminating region comprises an SV40 or protamine gene polyadenylation signal. In another preferred embodiment, a coding sequence comprises a cDNA insert.

In a preferred embodiment, a gene product is a polynucleotide. A preferred polynucleotide is an antisense molecule. A preferred antisense molecule is an antisense polynucleotide to c-myb.

In another embodiment, a gene product is a polypeptide. A preferred polypeptide is a growth factor. A preferred such growth factor is FGF-5, acidic FGF, basic FGF or PDGF. In other preferred embodiments, a polypeptide is dystropin, a mutant FGF receptor, a mutant PDGF receptor, a mutant I-CAM or a mutant V-CAM.

Delivering is preferably injecting an adenovirus vector construct directly into a cardiac or a vascular smooth muscle cell. In a particularly preferred embodiment, delivering is infusing an adenovirus vector construct into a blood vessel that perfuses a muscle cell.

An adenovirus vector construct is typically delivered as a pharmaceutical composition. Such a composition comprises a physiologically acceptable carrier and an effective expression-inducing amount of an adenovirus vector construct.

In yet another aspect, the present invention provides a process for preparing an adenovirus vector construct for use in transfecting a cardiac muscle cell or a vascular smooth muscle cell, which process comprises the steps of:

a) providing an adenovirus; and b) incorporating into that adenovirus a coding sequence that encodes a gene product desired for introduction into a cardiac muscle or vascular smooth muscle cell.

In yet another aspect, the present invention provides for an adenovirus vector construct produced in accordance with such a process.

DETAILED DESCRIPTION OF THE INVENTION

I. The Invention

The present invention addresses one or more shortcomings in the prior art through the provision of an adenovirus mediated process for regulating gene product expression in cardiac or vascular smooth muscle cells. In accordance with a process of this invention, an adenovirus vector construct is used to deliver a gene to those muscle cells and thus affect expression of that gene's product. Expression of the gene product thereby alters function of those cells and achieves a physiologically desirable effect. A process of the present invention can be used to regulate expression of a cardiac muscle cell or a vascular smooth muscle cell, whether that cell is situated in vitro, in situ, or in vivo in a living organism.

A. Process of Regulating Gene Product Expression in Cardiac Muscle Cell

In one aspect, the present invention provides a process of regulating gene product expression in a muscle cell of heart (i.e., a cardiac muscle cell or cardiac myocyte). In accordance with that process, an adenovirus vector construct comprising a coding sequence that encodes the gene product is delivered to a cardiac muscle cell. The cardiac muscle cell is then maintained under physiological conditions and for a period of time sufficient for the gene to enter the cardiac muscle cell, for the gene to be transcribed and for the product of that gene to be expressed.

1. Adenovirus Vector

The use of adenovirus as a vector for cell transfection is well known in the art. Adenovirus vector-mediated cell transfection has been reported for various cells (Stratford-Perricaudet, et al., 1992).

An adenovirus vector of the present invention is replication defective. A virus is rendered replication defective by deletion of the viral early gene region 1 (E1). An adenovirus lacking an E1 region is competent to replicate only in cells, such as human 293 cells, which express adenovirus early gene region 1 genes from their cellular genome. Thus, such an adenovirus cannot kill cells that do not express that early gene product.

In a preferred embodiment, an adenovirus vector used in the present invention is lacking both the E1 and the E3 early gene regions. Techniques for preparing replication defective adenoviruses are well known in the art (See. e.g. McGrory et al., 1988, and Gluzman et al., 1982).

It is believed that any adenovirus vector can be used in the practice of the present invention. Thus, an adenovirus vector can be of any of the 42 different known serotypes or subgroups A–F. Adenovirus type S of subgroup C is the preferred staring material for production of a replication-defective adenovirus vector.

An adenovirus is engineered to contain a coding DNA sequence for use as a vector. Such a recombinant adenovirus has been described by Gluzman et al., 1982. Individual DNA sequences such as cDNAs that encode a gene product are inserted into the adenovirus to create a vector construct.

In a preferred embodiment, therefore, a coding sequence for a gene product is introduced or incorporated into an adenovirus at the position from which the E1 coding sequences have been removed. However, the position of insertion within the adenovirus sequences is not critical to the present invention. A coding sequence can also be inserted in lieu of the delected E3 region in E3 replacement vectors as described previously by Karlsson et al. (1986). Preferably, the E1 region of adenovirus is replaced by the coding DNA sequence or gene.

The resulting adenovirus vector is co-transfected into 293 cells together with a plasmid carrying a complete adenovirus genome to propagate the adenovirus. An exemplary such plasmid is pJM17. Co-transfection is performed in accordance with standard procedures well known in the art. By way of example, 293 cells are cultured in Dulbecco's modified Eagle's medium containing fetal calf serum. Confluent cultures are split the day before calcium phosphate cotransfection of plasmids. After addition of the DNA to the cells, the cells are shocked (e.g., a 15% glycerol shock) to boost transfection efficiency and the cells are overlaid with agar in DMEM containing fetal calf serum, penicillin, streptomycin sulfate, and other antibiotics or antifungal agents as needed. Monolayers are incubated until virl plaques appear (about 5–15 days).

These plaques are picked, suspended in medium containing fetal calf serum, and used to infect a new monolayer of 293 cells. When greater than 90% of the cells showed infection, viral lysates are subjected to a freeze/thaw cycle and designated as primary stocks. The presence of recombinant virus is verified by preparation of viral DNA from infected 293 cells, restriction analysis, and Southern blotting. Secondary stocks are subsequently generated by infecting 293 cells with primary virus stock at a multiplicity of infection of 0.01 and incubation until lysis.

The particular cell line used to propagate the recombinant adenoviruses of the present invention is not critical to the present invention. Recombinant adenovirus vectors can be propagated on, e.g., human 293 cells, or in other cell lines that are permissive for conditional replication-defective adenovirus infection, e.g., those which express adenovirus E1 gene products "in trans" so as to complement the defect in a conditional replication-defective vector. Further, the cells can be propagated either on plastic dishes or in suspension culture, in order to obtain virus stocks thereof.

2. Coding Sequence

A coding sequence in an adenovirus vector can code for any gene product. In one embodiment, a gene product is a polynucleodde such as a DNA or a RNA molecule. In an especially preferred embodiment, a gene product is an antisense molecule and, more preferably, an antisense RNA molecule. In a particularly preferred embodiment, an antisense RNA is an antisense RNA to an oncogene and, preferably, the c-myb oncogene.

In another preferred embodiment, a gene product is a polypeptide. As used herein, the term "polypeptide" means a polymer of amino acids connected by amide linkages, wherein the number of amino acid residues can range from about 5 to about one million. Preferably, a polypeptide has from about 10 to about 1000 amino acid residues and, even more preferably from about 20 to about 500 amino residues. Thus, as used herein, a polypeptide includes what is often referred to in the art as an oligopeptide (5–10 amino acid residues), a polypeptide (11–100 amino acid residues) and a protein (>100 amino acid residues).

A polypeptide encoded by a coding sequence can undergo post-translational modification to form conjugates with carbohydrates, lipids, nucleic acids and the like to form glycopolypeptides (e.g. glycoproteins), lipopolypeptides (e.g. lipoproteins) and other like conjugates.

Any polypeptide can be encoded by a coding sequence of an adenovirus of the present invention. A coding sequence can comprise introns and exons so long as the coding sequence comprises at least one open reading frame for transcription, translation and expression of that polypeptide. Thus, a coding sequence can comprise a gene, a split gene or a cDNA molecule. In the event that the coding sequence comprises a split gene (contains one or more introns), a cell transformed or transfected with a DNA molecule containing that split gene must have means for removing those introns and splicing together the exons in the RNA transcript from that DNA molecule if expression of that gene product is desired.

In a preferred embodiment, a polypeptide encoded by a coding sequence of an adenovirus vector construct of the present invention alters the function of a cardiac or vascular smooth muscle cell exposed to that polypeptide. Exemplary and preferred polypeptides are growth factors such as an endothelial growth factor or a vascular smooth muscle growth factor; a growth factor receptor; dystropin or a cell adhesion molecule (CAM) such as a mutant I-CAM or V-CAM (Edelman, GM, 1983).

A preferred growth factor is a fibroblast growth factor (FGF) such as FGF-5, acidic FGF and basic FGF; or platelet derived growth factor (PDGF).

A preferred receptor is mutant PDGF receptor (See e.g., Fantl et al., 1989; Coughlin et al., 1990 and Escobedo et al., 1988) or mutant FGF receptor (See e.g., Peters et al., 1992; Mohammadi et al., 1992; Amaya et al., 1991 and Bellot et al., 1991).

3. Enhancer-Promoter

A coding sequence of an adenovirus vector construct is preferably operatively linked to an enhancer-promoter other than an adenovirus enhancer-promoter. A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linted" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cardiac or vascular smooth muscle cell. In an example set forth hereinafter, the human cytomegalovirus (CMV) immediate early gene promoter has been used to result in high-level expression of a gene. However, the use of other viral or mammalian cellular promoters which are well-known in the art is also suitable to achieve expression of the gene product provided that the levels of expression are sufficient to achieve a physiologic effect. Exemplary and preferred enhancer-promoters are the CMV promoter, the Rous sarcoma virus (RSV) promoter and the muscle-specific creatine kinase (MCK) enhancer (Zambetti et al., 1992; Yi et al., 1991 and Sternberg et al., 1988).

By employing an enhancer-promoter with well-known properties, the level and pattern of gene product expression can be optimized. For example, selection of an enhancer-promoter that is active specifically in cardiac cells permits tissue-specific expression of the gene product. A preferred cardiac muscle specific enhancer-promoter is a cardiac isoform troponin C (cTNC) promoter (See e.g., Parmacek et al., 1992 and Parmacek et al., 1990). Still further, selection of an enhancer-promoter that is regulated in response to a specific physiologic signal can permit inducible gene product expression.

4. Transcription-terminating Region

A coding sequence of an adenovirus vector construct is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Transcription-terminating regions are well known in the art. A preferred transcription-terminating region used in an adenovirus vector construct of the present invention comprises a polyadenylation signal of SV40 or the protamine gene.

5. Delivering

Means by which an adenovirus vector construct is delivered to a cardiac muscle cell depend upon whether that cardiac muscle cell is situated in vitro, in situ or in vivo. Where a cardiac muscle cell is in vitro, delivery of an adenovirus construct is preferably accomplished by (1) exposing that cell to medium that contains the adenovirus or (2) injecting the adenovirus vector construct into the muscle cell. In a preferred embodiment, delivering is injecting an adenovirus vector construct into a cardiac muscle cell. Where a cardiac muscle cell is situated in situ (e.g. in an intact heart), delivery is preferably accomplished by (1) perfusing the in situ preparation with a solution that contains an adenovirus vector construct or (2) injecting such a construct into a muscle (e.g. ventricle wall, atrial wall). Injection of a recombinant DNA molecule into the myocardium resulted in expression of the gene product encoded by that molecule (U.S. patent application Ser. No. 07/789,983).

As set forth in that patent application, a recombinant bacterial ,galactosidase gene under the control of a Rous sarcoma virus promoter was introduced into and expressed in adult rat cardiac myocytes in vivo by the injection of purified plasmid DNA directly into the left ventricular wall. Cardiac myocytes expressing the recombinant β-galactosidase activity were detected histochemically in rat heart for at least six months following injection of the recombinant β-galactosidase gene.

Only cardiac muscle cells were found to have taken up the vector and expressed β-gal. No expression of β-gal was observed in other cells in the heart such as fibroblasts or the cells lining the heart blood vessels. More than about 75 percent of the hearts receiving the injected DNA expressed the foreign gene, and this expression was stable for periods of at least six months.

By way of further example, the direct injection of a gene for fibroblast growth factor-5 (an angiogenesis factor gene) was associated with an increase in capillary number in the injected heart. Following injection of a recombinant plasmid comprising FGF-5 DNA, a 30–40 percent increase in the number of capillaries was observed in the injected heart wall as compared to hearts injected with control DNA solutions. Microscopic examination revealed that the structure of the capillaries in the injected hearts was normal.

Rats were injected with a plasmid-encoding human fibroblast growth factor-5 (hFGF-5) in an attempt to stimulate angiogenesis or collateral blood flow in the adult rat heart. Rats were sacrificed at 3 weeks following injection and capillary density was measured by computerized light microscopy. Rats injected with control vectors displayed approximately 2300 capillaries/mm$^2$ (p<0.001). Thus, direct injection of a fibroblast growth factor-5 expression vector stimulates collateral vessel formation in areas of injected myocardium.

Where a cardiac muscle cell is situated in vivo, delivery is preferably accomplished by (1) infusing an adenovirus vector construct into a blood vessel that perfuses the heart or (2) injecting an adenovirus vector construct directly into a heart muscle such as a ventricular or atrial wall. In an especially preferred in vivo embodiment, a catheter is inserted into a blood vessel in the neck of an organism and the tip of the indwelling catheter is advanced with fluoroscopic guidance to a position in a coronary artery or coronary sinus that perfuses a portion of the myocardium. It is preferred that the tip of an indwelling catheter be placed in proximity to an area of the heart that contains cardiac cells to be transfected. Thus, in one preferred embodiment, an indwelling catheter is inserted into either an external jugular vein or a carotid artery and the catheter is advanced until the tip of the catheter is situated in the coronary sinus ostium or left coronary artery. By way of example, where cardiac muscle cells were transfected with an adenovirus vector construct comprising a coding sequence for β-galactosidase (β-gal) by infusing that construct via a catheter placed into the left coronary artery or coronary sinus ostium, cardiac muscle cells expressed β-gal (See Examples 1 and 2 hereinafter).

After delivery of an adenovirus vector construct to a cardiac muscle cell, that cell is maintained under physiological conditions and for a period of time sufficient for the adenovirus vector construct to infect the cardiac cell and for cellular expression of a coding sequence contained in that construct.

Physiological conditions are those necessary for viability of the cardiac muscle cell and include conditions of temperature, pH, osmolality and the like. In a preferred embodiment, temperature is from about 20° C. to about 50° C., more preferably from about 30° C. to about 40° C. and, even more preferably about 37° C.

pH is preferably from about a value of 6.0 to a value of about 8.0, more preferably from about a value of about 6.8 to a value of about 7.8 and, most preferably about 7.4. Osmolality is preferably from about 200 milliosmols per liter (mosm/L) to about 400 mosm/l and, more preferably from about 290 mosm/L to about 310 mosm/L. Other physiological conditions needed to sustain cardiac muscle cell viability are well known in the art.

A time period sufficient for expression of a coding sequence in a cardiac cell varies inter alia as is well known in the art on the type of adenovirus vector used and the method of delivery. Where the adenovirus vector was derived from type 5 adenovirus and the virus vector was infused into a coronary artery, expression was observed 3 to 5 days after infusion (See Example 2 hereinafter).

It should also be pointed out that because the adenovirus vector employed in replication defective, it is not capable of replicating in the cells that are ultimately infected. Moreover, it has been found that the genomic integration frequency of adenovirus is usually fairly low. Thus, where continued treatment is required it may be necessary to reintroduce the virus every 6 months to a year. In these circumstances, it may therefore be necessary to conduct long term therapy, where expression levels are monitored at selected intervals.

An adenovirus vector construct is typically delivered in the form of a pharmacological composition that comprises a physiologically acceptable carrier and the adenovirus vector construct. An effective expression-inducing amount of an adenovirus vector construct is delivered. As used herein, the term "effective expression-inducing amount" means that number of virus vector particles necessary to effectuate expression of a gene product encoded by a coding sequence contained in that vector. Means for determining an effective expression-inducing amount of an adenovirus vector construct are well known in the art. An effective expression-inducing amount is typically from about $10^7$ plaque forming units (pfu) to about $10^{15}$ pfu, preferably from about $10^8$ pfu to about $10^{14}$ pfu and, more preferably, from about $10^9$ to about $10^{12}$ pfu.

As is well known in the art, a specific dose level for any particular subject depends upon a variety of factors including the infectivity of the adenovirus vector, the age, body weight, general health, sex, diet, time of administration, route of administration, rate of excretion, and the severity of the particular disease undergoing therapy.

In that adenovirus is a virus that infects humans, there can be certain individuals that have developed antibodies to certain adenovirus proteins. In these circumstances, it is possible that such individuals might develop an immunological reaction to the virus. Thus, where an immunological reaction is believed to be a possibility, one can first test the subject to determine the existence of antibodies. Such a test can be performed in a variety of accepted manners, for example, through a simple skin test or through a test of the circulating blood levels of adenovirus-neutralizing antibodies. In fact, under such circumstances, one may desire to introduce a test dose of on the order of $\times 10^6$ to $1 \times 10^6$ or so virus particles. Then, if no untoward reaction is seen, the dose is elevated over a period of time until the desired dosage is reached, such as through the administration of incremental dosages of approximately an order of magnitude.

B. Process of Regulating Gene Product Expression in a Vascular Smooth Muscle Cell In another aspect, the present invention provides a process of regulating gene product expression in a vascular smooth muscle cell (e.g. an arterial smooth muscle cell). In accordance with that process, an adenovirus vector construct comprising a coding sequence that encodes that gene product is delivered to a vascular smooth muscle cell. The vascular smooth muscle cell is then maintained under physiological conditions and for a period of time sufficient for the gene to enter the vascular smooth muscle cell, for the gene to be transcribed and for the product of that gene to be expressed. A preferred vascular smooth muscle cell is a coronary artery smooth muscle cell.

An adenovirus vector construct used in a process of regulating gene product expression in a vascular smooth muscle cell is the same as the construct discussed above relative to cardiac muscle. Similarly, an enhancer-promoter, a transcription terminating region and a coding sequence are the same as set forth above with the exception that a preferred enhancer-promoter for use with vascular smooth muscle is a vascular smooth muscle specific enhancer-promoter such as an endothelin promoter (See e.g., Lee, et al., 1990 and Bloch et al., 1989) or a smooth muscle α-actin promoter (See e.g., Foster et al., 1992 and Blank et al., 1992).

Delivering is preferably the same as set forth above in relation to cardiac muscle and depends upon whether the vascular smooth muscle cell is situated in situ, in vitro or in vivo.

C. Pharmaceutical Compositions

In another aspect, the present invention relates to a pharmaceutical composition wherein the adenovirus vector gene construct is dispersed in a physiologically acceptable solution or buffer.

A composition of the present invention is typically administered parenterally in dosage unit formulations containing standard, well known nontoxic physiologically acceptable carriers, adjuvants, and vehicles as desired. The term parenteral as used herein includes intravenous, intramuscular, intraarterial injection, or infusion techniques.

Injectable preparations, for example, sterile injectable aqueous or oleaginous suspensions are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminant, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

D. Process of Preparing an Adenovirus Vector Construct

In another aspect, the present invention provides a process of preparing an adenovirus vector construct for use in regulating gene product expression in a cardiac muscle or vascular smooth muscle cell. Such a process comprises the steps of:

a) providing an adenovirus; and b) incorporating into that adenovirus a coding sequence that encodes a gene product desired for introduction into a cardiac muscle or vascular smooth muscle cell.

A coding sequence is incorporated into an adenovirus using standard techniques well known in the art such that the gene product encoded by that sequence is expressed in a muscle cell infected with the adenovirus vector construct. In a preferred embodiment, a coding sequence is operatively linked to a non-adenovirus enhancer-promoter. Exemplary and preferred such enhancer-promoters are set forth above.

A gene product desired for introduction into a cardiac muscle or vascular smooth muscle cell is preferably the same as set forth above in relation to a process of regulating gene product expression in those cells.

In yet another aspect, the present invention provides for an adenovirus vector construct produced in accordance with such a process.

The following examples illustrate particular embodiments of the present invention and are not limiting of the specification and claims in any way.

EXAMPLE 1
Making of Adenovirus Vector Construct

This example describes the use of recombinant replication defective adenoviruses in the preparation of virus vector constructs comprising a coding DNA sequence.

Recombinant adenovirus (Gluzman et al., 1982) containing distinct cDNAs (AdCMV-cDNA) were prepared in accordance with standard techniques well known in the art. E. coli β-galactosidase cDNA carrying the SV40 T antigen nuclear targeting signal (Bonnerot et al., 1987) was inserted into pAdCMV to create a distinct construct comprising the cytomegalovirus (CMV) promoter, the β-Gal cDNA and a polyadenylation signal from either the SV40 virus or the mouse protamine gene, and flanked by adenovirus type 5 sequences. In this construct, the E1 and E3 region of adenovirus were deleted and the E1 region was replaced by the β-Gal encoding sequence.

The resulting plasmid, designated AdCMVβ-gal, was cotransfected into 293 cells. Co-transfection was performed as follows: 293 cells were cultured in Dulbecco's modified Eagle's medium (DMEM) containing 2% fetal calf serum. Confluent dishes were split to non-confluent flasks the day before cotransfection with pAdCMVβ-gal. Monolayers were incubated until the appearance of viral plaques.

These plaques were picked, suspended in DMEM containing 2% fetal calf serum and used to infect a new monolayer of 293 cells. When greater than 90% of the cells showed infection, viral lysates were subjected to a freeze/thaw cycle and were designated as primary stocks. Recombinant virus with the correct structure was verified by preparation of viral DNA from productively-infected 293 cells, restriction analysis, and Southern blotting. Secondary stocks were subsequently generated by infecting 293 cells with primary virus stock and incubation until lysis.

The large scale production of recombinant adenovirus was performed in 293 cells. Infected cells were lysed 48 hours post-infection. Virus-containing extracts were centrifuged to remove debris before precipitation of the virus. Virus was collected by centrifugation, resuspended in isotonic medium, purified, and sterilized.

Alternatively, precipitated virus can be resuspended in 50 mM Tris-HCl pH 7.8 containing CsCl (d=1.10 g/ml), layered over a step-gradient formed of 2 ml CsCl (d=1.40) and 3 ml of CsCl (d=1.30), and centrifuged 2 hours at 20,000 rpm at 10° C. in a Sorvall TH641 rotor. Virus is collected from the lower interface and dialyzed overnight at 4° C. versus isotonic saline.

EXAMPLE 2
Functional Expression of AdCMVβ-gal

Adult rabbits were anesthetized and a catheter was inserted into the right carotid artery or internal jugular vein. The tip of the catheter was advanced under fluoroscopic guidance to the left coronary artery or coronary sinus ostium.

About 1000 μg to 1500 μg of adenovirus vector construct pAdCMVβ-gal, prepared in accordance with the procedures of Example 1, were suspended in physiologically buffered saline. About $2 \times 10^9$ plaque forming units (pfu) of pAdCMVβ-gal were. infused into the indwelling catheter. The catheter was removed, all incisions were closed and the rabbits allowed to recover. Rabbits were killed 5 to about 21 days after injection. The heart and associated vasculature was removed and examined histochemically for β-gal activity as set forth below.

Three-millimeter cross sections of the left ventricle were fixed for 5 minutes at room temperature with 1.25% glutaraldehyde in PBS, washed three times at room temperature in PBS, and stained for β-galactosidase activity with X-gal (Biorad) for 4–16 hours as described by Nabel et al. (Nabel, et al., (1989). The 3-mm sections were embedded with glycomethocyrlate, and 4–7 μm sections were cut and counterstained with hematoxylin and eosin as described previously. (Nabel, et al., 1989). Photomicroscopy was performed using Kodak Ektachrome 200 file and Leitz Laborlux D and Wild M8 microscopes. β-Gal activity was observed in coronary vascular smooth muscle and in cardiac muscle cells.

EXAMPLE 3
Regulation of Dystropin Expression In Cardiac Cells of Subjects With Duchenne's Muscular Dystrophy A process of the present invention can be used in the treatment of human disorders via gene therapy, such as, for example, in the treatment of Duchenne's muscular dystrophy.

Human subjects with Duchenne's muscular dystrophy are initially tested for the presence of antibodies directed against an adenovirus used to prepare an adenovirus vector construct. If antibodies are present or if the patient has a history of allergy to other substances, that patient is preferably given a test dose of from about $10^3$ to about $10^6$ recombinant adenovirus particles.

Recombinant adenovirus comprising a coding sequence for dystropin is prepared and purified by any method that would be acceptable to the Food and Drug Administration for administration to human subjects and proven to have sufficient efficacy and purity for human use.

Adenovirus is administered to patients preferably by means of intravenous administration in any suitable pharmacological composition, either as a bolus or as an infusion over a period of time. An adenovirus is administered in an effective expression-inducing amount. Typically, it is believed that such an effective amount is from about $10^8$ to about $5 \times 10^{12}$ virus particles or pfu.

Patients would remain hospitalized during the trial to monitor acute and delayed adverse reactions such as an inflammatory reaction.

While the compositions and methods of this invention have been described in terms of preferred embodiments, it will be apparent to those of skill in the art that variations can be applied to the composition, process and in the steps or in the sequence of steps of the process described herein without departing from the concept, spirit and scope of the invention.

REFERENCES

The references listed below are incorporated herein by reference to the extent that they supplement, explain, provide a background for or teach methodology, techniques and/or compositions employed herein.

Amaya, E., Musci, T. J., Kirschner, M. W. (1991) *Cell* 66(2) 257–70

Bellot, F., Crumley G., Kaplow, J. M., Schlessinger, J., Jaye, M., Dionne, C.A. (1991) 10, 2849–54

Blank, R. S., McQuinn, T. C., Yin, K. C., Thompson, M. M., Takeyasu, K., Schwartz, R. J., Owens, G. K. (1992) *J. Biol. Chem.* 267(2) 984–989

Bloch, K. D., Friedrich, S. P., Lee, M. E., Eddy, R. L., Shows, T. B., Quertermous, T., (1989) *J. Biol. Chem.*, 264(18):10851–57

Bonnerot, C., Rocancourt, D., Briand, P., Grimber, G., and Nicolas, J. F. (1987) *Proc. Natl. Acad. Sci. USA*, 84, 6795–6799

Coughlin, S. R., Escobedo, J. A., Williams, L. T. (1990) *Science* 243(4895) 1191–4

Davis, C. G., Elhammer, A., Russell, D. W., Schneider, W. J., Kornfeld, S., Brown, M. S., and Goldstein, J. L. (1986) *J. Biol. Chem.,* 261, 2828–2838

Dichek, D. A., Bratthauer, G. L., Beg, Z. H., Anderson, K. D., Newman, K. D., Zwiebel, J. A., Hoeg, J. M., and Anderson, W. F. (1991) *Som. Cell. Mol. Gen.,* 17, 287–301

Edelman, G. M. (1983) *Science* 219(4584) 450–457

Escobedo, J. A., Williams, L. T. (1988) *Nature* 335(6185) 85–87

Fantl, W. J., Escobedo, J. A., Williams, L. T., (1989) *Mol. Cell Biol.* 4473–8 (1989)

Foster, D. N., Min, B., Foster, L. K., Stoflet, E. S., Sun, S., Getz, M. J., Strauch, A. R., (1992) *J. Biol. Chem.* 267(17) 11995–12003

Ghosh-Choudhury, G. and Graham, F. L. (1987) *Biochem. Biophys. Res. Comm.,* 147, 964–973

Gluzman, Y., Reichl, H., and Solnick, D. (1982) in *Eukaryotic Viral Vectors* (Gluzman, Y., ed) pp. 187–192, Cold Spring Harbor Press, Cold Spring Harbor, N.Y.

Graham, F. L., Smiley, J., Russell, W. C., and Nairn, R. (1977) *J. gen. Virol.,* 36, 59–72

Jaffe, H. A., Danel, C., Longenecker, G., Metzger, M., Setoguchi, Y., Rosenfeld, M. A., Gant, T. W., Thorgeirsson, S. S., Stratford-Perricaudet, L. D., Perricaudet, M., Pavirani, A., Lecocq, J.-P., and Crystal, R. G. (1992) *Nature Genetics,* 1, 372–378

Kay, M. A., Baley, P., Rothenberg, S., Leland, F., Fleming, L., Parker Ponder, K., Liu, T. -J., Finegold, M., Darlington, G., Pokorny, W., and Woo, S. L. C. (1992) *Proc. Natl. Acad. Sci. USA,* 89, 89–93

Karlsson, S., Van Doren, K., Schweiger, S. G., Nienhuis, A. W., and Gluzman, Y. (1986) *EMBO J.,* 5, 2377–2385.

Lee, M. E., Bloch, K. D., Clifford, J. A., Quertermous, T., (1990) *J. Biol. Chem.,* 265(18):10446–50

McGrory, W. J., Bautista, D. S., and Graham, F. L. (1988) *Virol.,* 163, 614–617

Mercola, M., Beininger, P. L., Shamah, S. M., Porter, J., Wang, C. Y., Stiles, C. D., (1990) *Gen. Dev.* 4(12B) 2333–41

Mohammadi, M., Dionne, C. A., Li, W., Li, N., Spivak, T., Honegger, A. M., Jaye, M., Schlessinger, J. (1992) *Nature* 358(6388) 681–4

Nabel E. G., Plautz G., Boyce F. M., Stanley J. C., Nabel G. J.: Recombinant gene expression in vivo within endothelial cells of the arterial wall. *Science* 244:1342–1344 (1989

Parmacek, M. S., Vora, A. J., Shen, T., Barr, E., Jung, F., Leiden, J. M. (1992) *Mol. Cell Biol.* 12(5) 1967–76

Parmacek, M. S., Bengur, A. R., Vora, A. J., Leiden, J. M., (1990) *J. Biol. Chem.* 265(26) 15970–76

Peters, K. G., Marie J., Wilson, E., Ives, H. E., Escobedo, J., Del Rosario, M., Mirda, D. (1992) *Nature* 358(6388) 678–81

Rosenfeld, M. A., Siegfried, W., Yoshimura, K., Yoneyama, K., Fukayama, M., Stier, L. E., Paäkko, P. K., Gilardi, P., Stratford-Perricaudet, L. D., Perricaudet, M., Jallat, S., Pavirani, A., Lecocq, J. -P., and Crystal, R. G. (1991) *Science,* 252, 431–434

Rosenfeld, M. A., Yoshimura, K., Trapnell, B. C., Yoneyama, K., Rosenthal, E. R., Dalemans, W., Fukayama, M., Bargon, J., Stier, L. E., Stratford-Perricaudet, L. D., Perricaudet, M., Guggino, W. B., Pavirani, A., Lecocq. J. -P., and Crystal, R. G. (1992) *Cell,* 68, 143–155

Roy Chowdhury, J., Grossman, M., Gupta, S., Roy Chowdhury, N., Baker, J. R., and Wilson, J. M. (1991) *Science,* 254, 1802

Sambrook, J., Fritsch, E. F., and Maniatis, T. (1989) *Molecular cloning: A laboratory manual,* Cold Spring Harbor Laboratory Press, New York Steinberg, E. A., Spizz, G., Perry W. M., Vizard, D., Weil, T., Olson, E. N. (1988) 8(7) 2896–909

Stratford-Perricaudet, L. D., Levrero, M., Chasse, J. -F., Perricaudet, M., and Briand, P. (1990) *Hum. Gene Ther.,* 1, 241–256

Stratford-Perricaudet, L. D., Makeh, I., Perricaudet, M., and Briand, P. (1992) *J. Clin. Invest.,* 90, 626–630

Talarico, D., Basilico, C. (1991) *Mol. Cell. Biol.* 2, 1138–45 van Doren, K. and Gluzman, Y. (1984) *Mol. Cell. Biol.,* 4, 1653–1656 van Doren, K., Hanahan, D., and Gluzman, Y. (1984) *J. Virol.,* 50, 606–614

Wilson, J. M., Grossman, M., Wu, C. H., Roy Chowdhury, N., Wu, G. Y., and Roy Chowdhury, J. (1992) *J. Biol. Chem.,* 267, 963–967

Wilson, J. M., Jefferson, D. M., Roy Chowdhury, J., Novikoff, P. M., Johnston, D. E., and Mulligan, R. C. (1988) *Proc. Natl. Acad. Sci. USA,* 85, 3014–3018

Wilson, J. M., Johnston, D. E., Jefferson, D. M., and Mulligan, R. C. (1988) *Proc. Natl. Acad. Sci. USA,* 85, 4421–4425

Wolfe, J. H., Deshmane, S. L., and Fraser, N. W. (1992) *Nature Genetics,* 1, 379–384

Yi, T. M., Walsh, K., Schimmel, P., (1991) *Nucleic Acids Res.* 19(11) 3027–33

Yokode, M., Pathak, R. K., Hammer, R. E., Brown, M. S., Goldstein, J. L., and Anderson, R. G. W. (1992) *J. Cell Biol.,* 117, 39–46

Zambetti, G. P., Bargonetti, J., Walker, K., Drives, C., Levine, A. U. (1992) *Genes Dev.* 6(7) 1143–52

What is claimed is:

1. A method for delivering a nucleic acid encoding a gene product to a cardiac muscle cell or vascular smooth muscle cell comprising injecting into myocardium or vascular smooth muscle an effective expression-inducing amount of a replication-deficient adenovirus vector operatively linked to a coding sequence that encodes the gene product wherein said gene product is expressed in said cardiac muscle cell or said vascular smooth muscle cell.

2. The method of claim 1 wherein said gene product is a protein competent to induce collateral blood vessel formation.

3. The method of claim 2 wherein said gene product encodes an angiogenesis factor.

4. The method of claim 1 wherein said vector is injected directly into a ventricle or atrial wall of the heart.

5. The method of claim 1 wherein about $10^7$ to $10^{15}$ plaque forming units of said vector are injected into the myocardium or said muscle.

6. The method of claim 5 wherein about $10^8$ to $10^{14}$ plaque forming units of said vector are injected into the myocardium or said muscle.

7. The method of claim 5 wherein about $10^9$ to $10^{12}$ plaque forming units of said vector are injected into the myocardium or said muscle.

8. The method of claim 1 wherein said replication-deficient adenovirus virus lacks the early gene region E1.

9. The method of claim 1 wherein said replication deficient adenovirus virus lacks the early gene region E3.

10. The method of claim 1 wherein said gene product encodes a growth factor.

11. The method of claim 10 wherein said growth factor is a fibroblast growth factor or a platelet derived growth factor.

12. The method of claim 11 wherein said fibroblast growth factor is acidic FGF, basic FGF, or FGF-5.

13. The method of claim 1 wherein said gene product is an endothelial growth factor or a vascular smooth muscle growth factor.

14. The method of claim 1 wherein said gene product is an antisense molecule.

15. The method according to claim 14 wherein said antisense molecule is a c-myb antisense molecule.

16. The process according to claim 1 wherein the coding sequence is operatively linked to cardiac muscle-specific enhancer promoter.

17. The method according to claim 16 wherein said cardiac muscle-specific enhancer-promoter is a cTNC promoter.

18. The method according to claim 1 wherein said coding sequence is encoded by cDNA or genomic DNA.

19. The method according to claim 1 wherein said coding sequence is operatively linked to an enhancer-promoter other than an adenovirus enhancer-promoter.

20. The method according to claim 19 wherein said enhancer-promoter is a cytomegalovirus promoter, an SV40 early promoter, a RSV promoter or an MCK enhancer.

21. The method according to claim 19 wherein said enhancer-promoter is specific for vascular smooth muscle.

22. The method according to claim 21 wherein said vascular smooth muscle specific enhancer-promoter is an endothelin promoter or a smooth muscle or actin promoter.

23. The method according to claim 1 wherein said adenovirus is adenovirus type 5.

24. The method according to claim 1 wherein said adenovirus lacks the early gene regions E1 and E3.

25. The method according to claim 1 wherein said adenovirus is adenovirus type 5 that lacks the early gene region E1.

26. The method according to claim 1 wherein said gene product is a polynucleotide.

27. The method according to claim 1 wherein said gene product is a polypeptide.

28. The method according to claim 27 wherein said polypeptide is a growth factor receptor, a cell adhesion molecule or dystrophin.

29. The method according to claim 28 wherein said growth factor receptor is a mutant FGF receptor or a mutant PDGF receptor.

30. The method according to claim 28 wherein said cell adhesion molecule is a mutant I-CAM or mutant V-CAM.

31. The method according to claim 1 wherein said vector is reintroduced at a selected interval.

32. The method according to claim 31 wherein said interval is from about 6 months to about one year.

33. A method of transforming a vascular smooth muscle cell with a polynucleotide comprising injecting an adenovirus vector containing the polynucleotide into vascular smooth muscle to thereby transform vascular smooth muscle cells.

34. A method of transforming a cardiac muscle cell with a polynucleotide comprising injecting an adenovirus vector containing the polynucleotide into myocardium to thereby transform cardiac muscle cells.

* * * * *